United States Patent
Trotter et al.

(10) Patent No.: US 11,241,574 B2
(45) Date of Patent: Feb. 8, 2022

(54) SYSTEMS AND METHODS FOR PROVIDING AND COORDINATING VAGUS NERVE STIMULATION WITH AUDIO THERAPY

(71) Applicant: Bose Corporation, Framingham, MA (US)

(72) Inventors: John Trotter, Sudbury, MA (US); Kathleen Kremer, Southborough, MA (US); Harsh Anilkant Mankodi, Brighton, MA (US)

(73) Assignee: Bose Corporation, Framingham, MA (US)

( * ) Notice: Subject to any disclaimer, the term of this patent is extended or adjusted under 35 U.S.C. 154(b) by 281 days.

(21) Appl. No.: 16/567,116

(22) Filed: Sep. 11, 2019

(65) Prior Publication Data
US 2021/0069488 A1    Mar. 11, 2021

(51) Int. Cl.
*A61N 1/04* (2006.01)
*A61N 1/36* (2006.01)

(52) U.S. Cl.
CPC ....... *A61N 1/0472* (2013.01); *A61N 1/36017* (2013.01); *A61N 1/36036* (2017.08); *A61N 1/36038* (2017.08); *A61N 1/36031* (2017.08)

(58) Field of Classification Search
CPC ............ A61N 1/36036; A61N 1/36038; A61N 1/0456
See application file for complete search history.

(56) References Cited

U.S. PATENT DOCUMENTS

| 4,503,863 A | 12/1985 | Katims |
| 7,613,519 B2 | 11/2009 | De Ridder |
| 7,725,195 B2 | 5/2010 | Lima et al. |
| 7,797,042 B2 | 9/2010 | Dietrich et al. |

(Continued)

FOREIGN PATENT DOCUMENTS

| CN | 103908747 B | 7/2014 |
| CN | 103961794 A | 8/2014 |

(Continued)

OTHER PUBLICATIONS

International Search Report and the Written Opinion of the International Searching Authority, International Patent Application No. PCT/US2020/050294, pp. 1-13, dated Nov. 19, 2020.

(Continued)

*Primary Examiner* — Alyssa M Alter
(74) *Attorney, Agent, or Firm* — Bond, Schoeneck & King, PLLC (57) ABSTRACT

A method of providing vagus nerve stimulation to a user is provided. The method includes the step of prompting, via a first audio cue emitted by an earpiece worn by a user, the user to inhale at a first point in time. The method may further include the step of prompting, via a second audio cue emitted by the earpiece, the user to exhale at a second point in time. The method may further include the step of stimulating a vagus nerve of the user with a first electrical signal generated by the earpiece at the second point in time. The first electrical signal may be applied to a concha of an ear of the user. The first electrical signal may be applied to an ear (Continued)

canal of the user. The first electrical signal may be applied to a tragus of the user.

20 Claims, 3 Drawing Sheets

(56) References Cited

U.S. PATENT DOCUMENTS

| | | |
|---|---|---|
| 8,262,717 B2 | 9/2012 | Rogers et al. |
| 8,506,469 B2 | 8/2013 | Dietrich et al. |
| 8,591,419 B2 | 11/2013 | Tyler |
| 8,666,501 B2 | 3/2014 | Kilgard et al. |
| 8,696,724 B2 | 4/2014 | Rogers |
| 8,885,861 B2 | 11/2014 | Beck et al. |
| 9,333,334 B2 | 5/2016 | Jeffery et al. |
| 9,610,443 B1 | 4/2017 | Dean et al. |
| 9,782,584 B2 | 10/2017 | Cartledge et al. |
| 2003/0195588 A1 | 10/2003 | Fischell et al. |
| 2003/0199945 A1 | 10/2003 | Ciulla |
| 2007/0027504 A1 | 2/2007 | Barrett |
| 2007/0260285 A1 | 11/2007 | Libbus et al. |
| 2007/0287931 A1* | 12/2007 | Dilorenzo ............ A61B 5/4094 600/545 |
| 2008/0021517 A1 | 1/2008 | Dietrich |
| 2008/0051852 A1 | 2/2008 | Dietrich et al. |
| 2010/0057154 A1 | 3/2010 | Dietrich et al. |
| 2011/0046432 A1 | 2/2011 | Simon et al. |
| 2011/0130615 A1 | 6/2011 | Mishelevich |
| 2011/0178442 A1 | 7/2011 | Mishelevich |
| 2012/0330373 A1 | 12/2012 | Ternes et al. |
| 2013/0066350 A1 | 3/2013 | Mishelevich |
| 2014/0067021 A1 | 3/2014 | Rezai et al. |
| 2014/0142669 A1 | 5/2014 | Cook et al. |
| 2015/0126802 A1 | 5/2015 | Lim et al. |
| 2016/0287898 A1 | 10/2016 | Smith et al. |
| 2016/0346545 A1 | 12/2016 | Pal et al. |
| 2017/0087364 A1* | 3/2017 | Cartledge ............ A61N 1/3603 |
| 2017/0143550 A1 | 5/2017 | Kilgard et al. |
| 2017/0151436 A1 | 6/2017 | Flaherty et al. |
| 2017/0368329 A1 | 12/2017 | Tyler et al. |
| 2018/0001077 A1 | 1/2018 | Cook et al. |
| 2018/0169411 A1 | 6/2018 | Goodall et al. |
| 2018/0169412 A1 | 6/2018 | Goodall et al. |
| 2018/0193641 A1 | 7/2018 | Black et al. |
| 2018/0200522 A1 | 7/2018 | Taca, Jr. |
| 2018/0250511 A1 | 9/2018 | Black et al. |
| 2018/0339148 A1 | 11/2018 | Kong |
| 2019/0001117 A1 | 1/2019 | Ben-David et al. |

FOREIGN PATENT DOCUMENTS

| | | |
|---|---|---|
| CN | 104055625 A | 9/2014 |
| CN | 203915230 U | 11/2014 |
| CN | 107041809 A | 8/2017 |
| CN | 107041810 A | 8/2017 |
| CN | 206660005 U | 11/2017 |
| CN | 107970087 A | 5/2018 |
| DE | 102005003735 | 7/2006 |
| DE | 202015007965 U1 | 12/2015 |
| EP | 2776121 A1 | 9/2014 |
| EP | 3377012 A1 | 9/2018 |
| KR | 101468355 B1 | 12/2014 |
| KR | 101724560 B1 | 4/2017 |
| WO | 2012139603 A1 | 10/2012 |
| WO | 2012168543 A1 | 12/2012 |
| WO | 2016176668 A1 | 11/2016 |
| WO | 2016196635 A2 | 12/2016 |
| WO | 2017171219 A1 | 10/2017 |
| WO | 2017173331 A1 | 10/2017 |
| WO | 2018071630 | 4/2018 |
| WO | 2018111997 A2 | 6/2018 |
| WO | 2019005//4 A1 | 1/2019 |

OTHER PUBLICATIONS

Pei-Jing Rong et al: "Transcutaneous vagus nerve stimulation for the treatment of depression: a study protocol for a double blinded randomized clinical trial", BMC Complementary and Alternative Medicine, Biomed Central Ltd., London, GB, vol. 12, No. 1, Dec. 14, 2012 (Dec. 14, 2012), p. 255, XP021135927, ISSN: 1472-6882, DOI: 10.1186/1472-6882-12-255.

Enterprise Neurotechnology Solutions; EMOTIV MN8; website available at: https://www.emotiv.com/workplace-wellness-safety-and-productivity-mn8/; last accessed Sep. 23, 2019.

* cited by examiner

SYSTEMS AND METHODS FOR PROVIDING AND COORDINATING VAGUS NERVE STIMULATION WITH AUDIO THERAPY

BACKGROUND

This disclosure generally relates to methods and systems for providing and coordinating vagus nerve stimulation (VNS) with audio therapy.

SUMMARY

This disclosure is directed to methods and systems for providing and coordinating vagus nerve stimulation (VNS) with audio therapy.

In one aspect, a method of providing VNS to a user is provided. The method includes the step of prompting, via a first audio cue emitted by an earpiece worn by a user, the user to inhale at a first point in time. The method may further include the step of prompting, via a second audio cue emitted by the earpiece, the user to exhale at a second point in time. The method may further include the step of stimulating a vagus nerve of the user with a first electrical signal generated by the earpiece at the second point in time. The first electrical signal may be applied to a concha of an ear of the user. The first electrical signal may be applied to an ear canal of the user. The first electrical signal may be applied to a tragus of the user.

According to an example, the method may further include the step of prompting, via a third audio cue emitted by the earpiece, the user to inhale at a third point in time. The method may further include the step of prompting, via a fourth audio cue emitted by the earpiece, the user to exhale at a fourth point in time. The method may further include the step of stimulating the vagus nerve of the user with a second electrical signal generated by the earpiece at the fourth point in time. A time period between the third and fourth points in time may be greater than a time period between the first and second points in time.

According to an example, the first and second audio cues may be verbal commands. The first and second audio cues may be audio tones. The first audio cue may be an inhalation recording. The second audio cue may be an exhalation recording.

According to an example, the method may further include the step of measuring, via a sensor, a biometric property of the user. The second point in time may be adjusted according to the biometric property. The biometric property may be heart rate variability. The biometric property may be respiration rate.

According to an example, the method may further include the step of prompting, via a fifth audio cue emitted by the earpiece, the user to inhale at a fifth point in time. The method may further include prompting, via a sixth audio cue emitted by the earpiece, the user to exhale at a sixth point in time. The method may further include stimulating the vagus nerve of the user with a third electrical signal generated by the earpiece at the sixth point in time. A time period between the fifth and sixth points in time may be greater than the time period between the third and fourth points in time. A time period between the third and fourth points in time may be greater than a time period between the first and second points in time.

According to an example, the method may further include the step of inputting, by the user via a user interface, one or more personal characteristics. The method may further include the step of adjusting a time period between the first point in time and the second point in time according to the one or more personal characteristics.

In another aspect, a system for providing VNS to a user is provided. The system may include an earpiece. The earpiece may include an audio transducer. The earpiece may include a first electrode. The earpiece may be configured to form a first electrical contact between the electrode and an ear canal, tragus, or concha of a first ear of a user. The earpiece may be further configured to emit a first audio cue from the audio transducer at a first point in time. The first audio cue may prompt the user to inhale. The earpiece may be further configured to emit a second audio cue from the audio transducer at a second point in time. The second audio cue may prompt the user to exhale. The earpiece may be configured to deliver a VNS signal to the user via the first electrode at the second point in time. The system may further include a second electrode. The second electrode may be configured to form a second electrical contact with the user.

According to an example, the earpiece may further include the second electrode. Alternatively, the second electrode may be incorporated into a second earpiece or other device.

According to an example, the second electrode may be configured to form the second electrical contract with the ear canal, tragus, or concha of the first ear of the user. In an alternative example, the second electrode may form the second electrical contact with an ear canal, tragus, or concha of a second ear of the user. In another alternative example, the second electrode may form the second electrical contact on a back portion of an earlobe of the first ear.

According to an example, the system may further include a sensor configured to measure a biometric property of the user.

According to an example, the system may further include a user interface configured for the user to input one or more personal characteristics.

In another aspect, an earpiece for providing VNS to a user is provided. The earpiece may include an audio transducer. The audio transducer may be configured to emit a first audio cue from the audio transducer at a first point in time. The first audio cue may prompt the user to inhale. The audio transducer may be configured to emit a second audio cue from the audio transducer at a second point in time. The second audio cue may prompt the user to exhale. The earpiece may further include a first electrode. The first electrode may be configured to form a first electrical contact with an ear canal, tragus, or concha of a user. The first electrode may be further configured to deliver a vagus nerve stimulation signal to the user via the first electrode at the second point in time.

According to an example, the earpiece may further include a second electrode configured to form a second electrical contact with the user.

According to an example, the earpiece may further include a sensor configured to measure a biometric property of the user.

In another aspect, a method of providing VNS to a user is provided. The method may include the steps of delivering, via an earpiece worn by a user, audio content to a user. The method may include stimulating a vagus nerve of the user with one or more electrical signals generated by the earpiece in coordination with the delivery of the audio content.

According to an example, the audio content may include guided breathing instructions prompting the user to adjust their respiration rate. The guided breathing instructions may include audio cues to prompt the user to adjust their respiration rate. The step of stimulating the vagus nerve of the user may further include stimulating the vagus nerve of the user in coordination with the audio cues.

According to an example, the method may further include the step of measuring, via a sensor, a biometric property of the user. The method may further include the step of adjusting the guided breathing instructions based on the biometric property. The guided breathing instructions may include audio cues to prompt the user to adjust their respiration rate. Playback timing of the audio cues may be adjusted based on the biometric property.

In another aspect, a system for providing VNS to a user is provided. The system may include an earpiece. The earpiece may include an audio transducer. The earpiece may include a first electrode. The earpiece may be configured to form a first electrical contact between the electrode and an ear canal, tragus, or concha of a first ear of a user. The earpiece may be further configured to deliver audio content to a user. The earpiece may be further configured to stimulate a vagus nerve of the user with one or more electrical signals generated by the earpiece in coordination with the delivery of the audio content. The system may further include a second electrode configured to form a second electrical contact with the user.

According to an example, the audio content may include guided breathing instructions prompting the user to adjust their respiration rate. The guided breathing instructions may include audio cues to prompt the user to adjust their respiration rate. The earpiece may be further configured to stimulate the vagus nerve of the user in coordination with the audio cues.

According to an example, the system may further include a sensor. The sensor may be configured to measure a biometric property of the user.

According to an example, the earpiece may be further configured to adjust the guided breathing instructions based on the biometric property. The guided breathing instructions may include audio cues to prompt the user to adjust their respiration rate. Playback timing of the audio cues may be adjusted based on the biometric property.

In another aspect, an earpiece for providing VNS to a user is provided. The earpiece may include an audio transducer. The audio transducer may be configured to deliver audio content to a user. The earpiece may further include a first electrode. The first electrode may be configured to form a first electrical contact with an ear canal, tragus, or concha of a user. The first electrode may be further configured to stimulate a vagus nerve of the user with one or more electrical signals generated by the earpiece in coordination with the delivery of the audio content.

According an example, the audio content may include guided breathing instructions prompting the user to adjust their respiration rate. The guided breathing instructions may include audio cues to prompt the user to adjust their respiration rate. The first electrode may be further configured to stimulate the vagus nerve of the user in coordination with the audio cues.

According to an example, the earpiece may be further configured to adjust the guided breathing instructions based on a biometric property of the user measured by a sensor. The guided breathing instructions may further include audio cues to prompt the user to adjust their respiration rate. Playback timing of the audio cues may be adjusted based on the biometric property.

Other features and advantages will be apparent from the description and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various examples.

DETAILED DESCRIPTION

This disclosure is directed to methods and systems for providing and coordinating vagus nerve stimulation (VNS) with audio therapy. VNS is a medical treatment that involves delivering electrical impulses to the vagus nerve of a user. The electrical impulses may be delivered via an ear canal, tragus, and/or concha of the user. VNS has been used to treat physiological disorders such as, for example, depression, insomnia, and tinnitus, among others. This disclosure relates generally to providing VNS in conjunction with an audio therapy regimen to help relieve insomnia or anxiety. The audio therapy may be, but is not limited to, guided breathing or binaural beats. In one example, the user follows a guided breathing regimen based on a soundtrack played through a set of earpieces. The soundtrack may include audio cues for the user to follow to guide their respiration rate. The earpieces may also carry electrodes for delivering VNS treatment in or around the ears of the user. As the user follows the guided breathing audio cure, VNS may be applied and controlled such that treatment is delivered based upon the cadence of the audio cues and/or the user's corresponding respiration rate.

The examples and implementations disclosed or otherwise envisioned herein can be utilized with any suitable earpiece. Examples of suitable earpieces include Bose® Sleepbuds™ (manufactured by Bose Corporation of Framingham, Mass.), ear tips, earbuds, in-ear headphones, over-the-ear headphones, noise-blocking earplugs, and hearing aids. However, the disclosure is not limited to these devices, and thus the disclosure and embodiments disclosed herein can encompass any earpiece configured to be placed at least partially within human ears.

Figure 1:
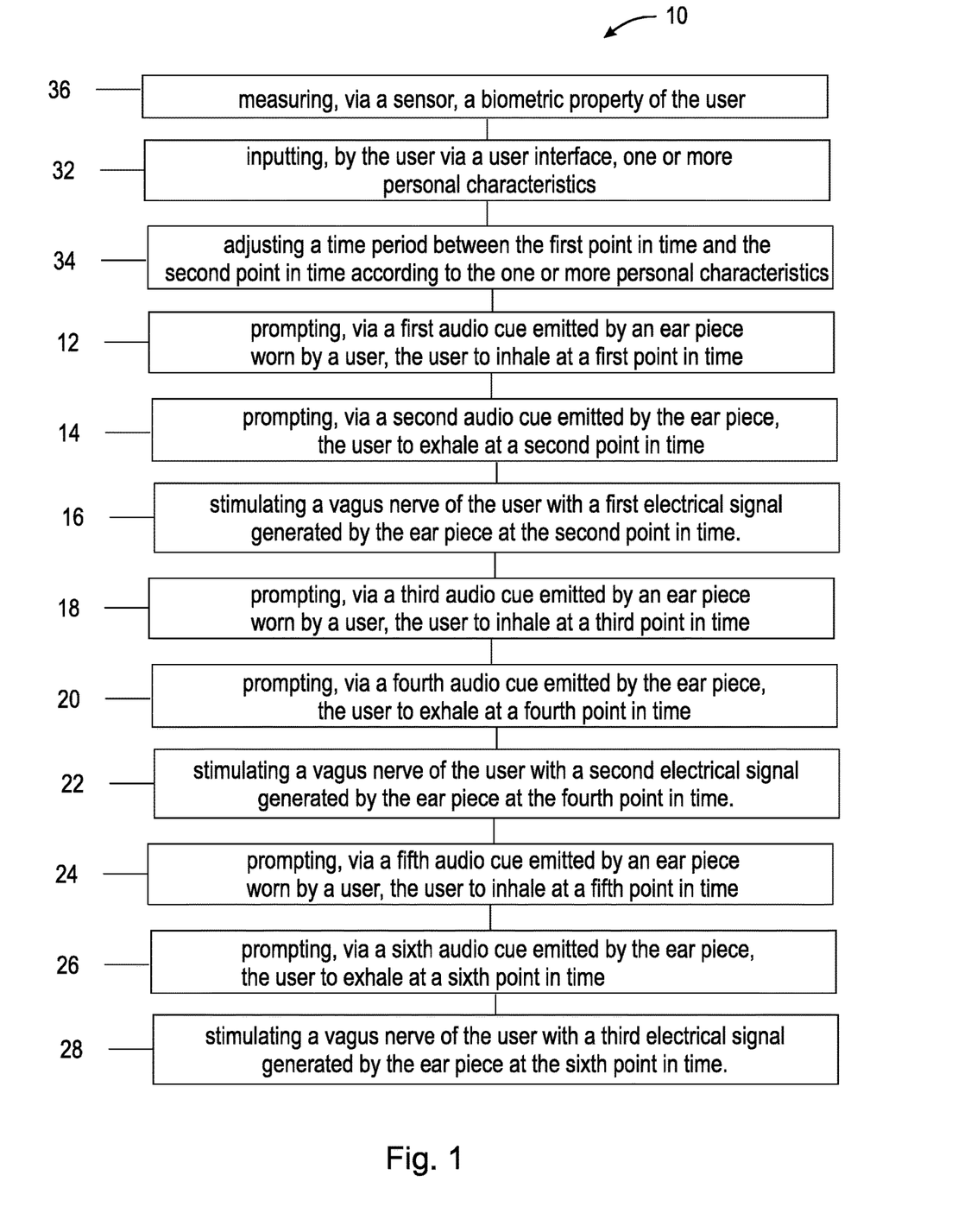
FIG. 1 is a flowchart of an example of a method of providing VNS to a user.

In one aspect, and with reference to FIG. 1, a method 10 of providing VNS to a user is provided. The method 10 includes the step of prompting 12, via a first audio cue emitted by an earpiece worn by a user, the user to inhale at a first point in time. The method 10 may further include the step of prompting 14, via a second audio cue emitted by the earpiece, the user to exhale at a second point in time. The method 16 may further include the step of stimulating a vagus nerve of the user with a first electrical signal generated by the earpiece at the second point in time. By following this method 10, the VNS signal may be applied simultaneously (at the second point in time) to the exhalation of the user for optimum therapeutic impact. In other examples, the method 10 may be altered to delay stimulation the vagus nerve until sometime after exhalation.

The first electrical signal (and any other electrical signal applied using method 10) may be applied to an ear canal of the user. The ear canal is considered to be the pathway running from the outer ear to the middle ear. The first electrical signal may also be applied to a concha of an ear of the user. The concha is considered to be the hollow area of the ear next to the ear canal. The first electrical signal may further be applied to a tragus of the user. The tragus is considered to be the small pointed eminence of the external ear, positioned in front of the concha, and projecting backwards over the meatus. The first electrical signal may also be applied to other areas of the user through which the vagus nerve may be stimulated by an electrical signal.

According to an example, the first and second audio cues may be verbal commands. The first and second audio cues may be audio tones. The first audio cue may be an inhalation recording. The second audio cue may be an exhalation recording. The first and second audio cue may also be any other sound to aid the user's guided breathing. The first and second audio cue may be the same or different, depending on the application. The first and second audio cue may be pre-recorded audio tracks, or they may be audio tones generated by the internal circuitry of the earpiece.

According to an example, the method 10 may further include the step of prompting 18, via a third audio cue emitted by the earpiece, the user to inhale at a third point in time. The method 10 may further include the step of prompting 20, via a fourth audio cue emitted by the earpiece, the user to exhale at a fourth point in time. The method 10 may further include the step of stimulating 22 the vagus nerve of the user with a second electrical signal generated by the earpiece at the fourth point in time. A time period between the third and fourth points in time may be greater than a time period between the first and second points in time. The increase in time periods between inhalation and exhalation may be used for sleep therapy guided breathing. The increase in time periods may be controlled by an algorithm processing biometric information of the user.

Similarly, the method 10 may further include the step of prompting 24, via a fifth audio cue emitted by the earpiece, the user to inhale at a fifth point in time. The method 10 may further include prompting 26, via a sixth audio cue emitted by the earpiece, the user to exhale at a sixth point in time. The method 10 may further include stimulating 22 the vagus nerve of the user with a third electrical signal generated by the earpiece at the sixth point in time. A time period between the fifth and sixth points in time may be greater than the time period between the third and fourth points in time. A time period between the third and fourth points in time is greater than a time period between the first and second points in time. As the user's respiration rate decreases over the course of the guided breathing regimen. VNS may no longer be applied at every exhalation. Further, as the user gets closer to the optimum relaxation or sleep state, VNS may stop entirely.

According to an example, the method 10 may further include the step of measuring 36, via a sensor, a biometric property of the user. The second point in time may be adjusted according to the biometric property. The biometric property may be any property which would impact the rate of optimum application of VNS. The biometric property may be heart rate variability. The biometric property may be respiration rate. For example, as the respiration rate of the user decreases over time, the rate guided breathing audio cues and corresponding VNS may similarly decrease. In addition to the second point in time, any other point in time of the audio therapy regimen may be adjusted according to the biometric property.

According to an example, the method 10 may further include the step of inputting 32, by the user via a user interface, one or more personal characteristics. These personal characteristics may include weight, age, or any other characteristics which would impact the rate of optimum application of VNS. The method may further include the step of adjusting a time period between the first point in time and the second point in time according to the one or more personal characteristics. In addition to the second point in time, any other point in time of the audio therapy regimen may be adjusted according to the biometric property.

Figure 2:
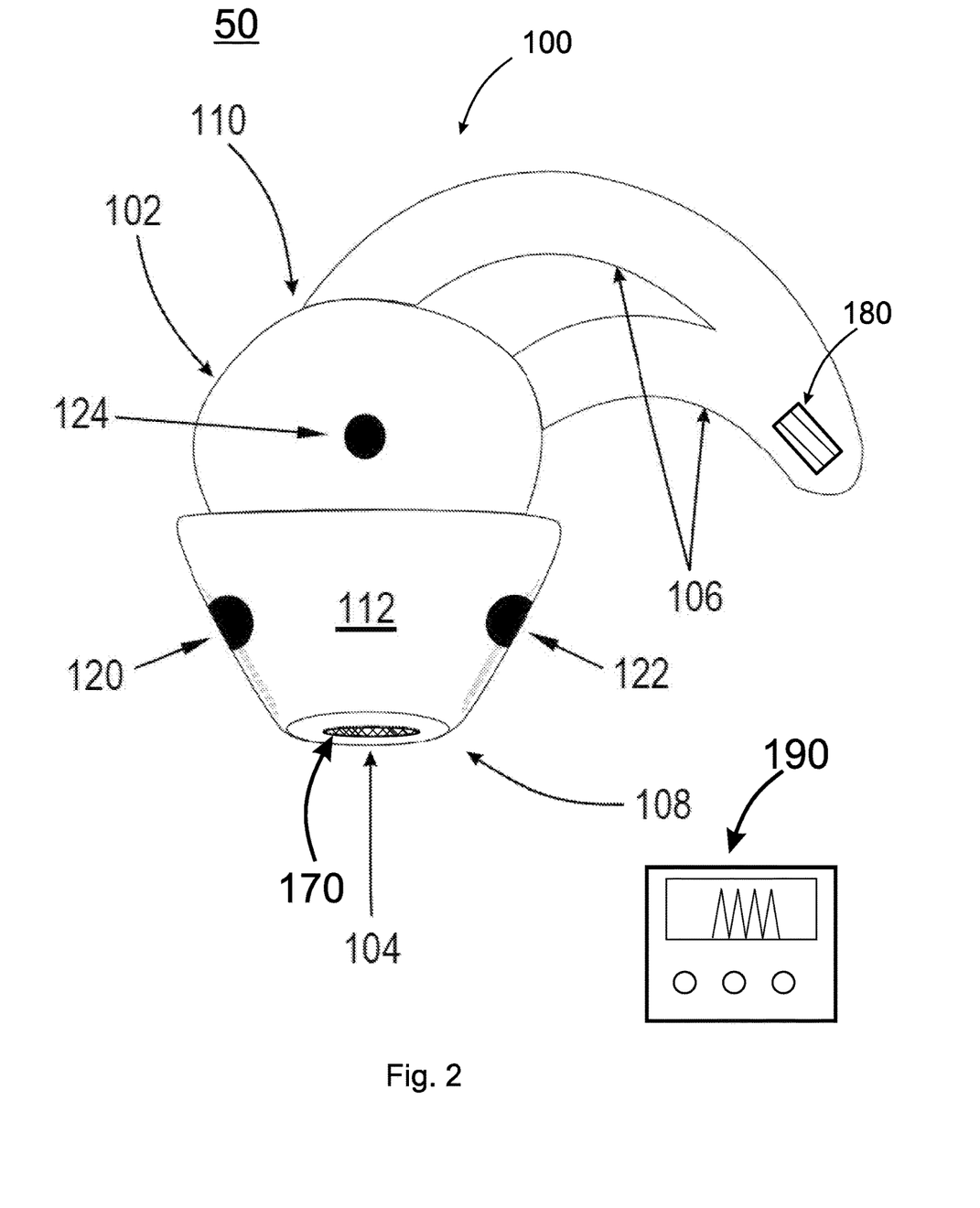
FIG. 2 is an example earpiece.

In another aspect, and with reference to FIG. 2, a system 50 for providing VNS to a user is provided. The system may include an earpiece 100. The earpiece 100 may include an audio transducer 170. An example audio transducer 170 is shown disposed within hollow passage 104.

The earpiece 100 may include a first electrode 120. The earpiece 100 may be configured to form a first electrical contact between the electrode 120 and an ear canal, tragus, or concha of a first ear of a user.

The earpiece 100 may be further configured to emit a first audio cue from the audio transducer 170 at a first point in time. The first audio cue may prompt the user to inhale. The earpiece 100 may be further configured to emit a second audio cue from the audio transducer 170 at a second point in time. The second audio cue may prompt the user to exhale. The first and second audio cues may be verbal commands. The first and second audio cues may be audio tones. The first audio cue may be an inhalation recording. The second audio cue may be an exhalation recording. The first and second audio cue may also be any other sound to aid the user's guided breathing. The first and second audio cue may be the same or different, depending on the application. The first and second audio cue may be pre-recorded audio tracks, or they may be audio tones generated by the internal circuitry of the earpiece.

The earpiece 100 may be configured to deliver a VNS signal to the user via the first electrode 120 at the second point in time. The system 100 may further include a second electrode 122. The second electrode 122 is used to complete a circuit with the first electrode and the stimulated portion of the user's ear. The second electrode 122 may be configured to form a second electrical contact with the user. According to an example, and as shown in FIG. 2 the earpiece 122 may include the both the first electrode 120 and the second electrode 122.

According to an example, the second electrode 122 may be configured to form the second electrical contract with the ear canal, tragus, or concha of the first ear of the user. As shown in FIG. 2, both the first electrode 120 and the second electrode 122 are positioned to make electrical contact with the same ear canal of the user when the earpiece 100 is properly worn. A third electrode 124 may also be incorporated. This third electrode 124 may be configured to form an electrical contact with a different portion of the ear than the second 122 electrode, such as the concha or tragus. It should be understood that to properly deliver a VNS signal to the user, only two electrodes may be active at once.

The second electrode 122 may form the second electrical contact with an ear canal, tragus, and/or concha of a second ear of the user. In this example, the second electrode may be incorporated into a second earpiece. In another alternative example, the second electrode 122 may form the second electrical contact on a back portion of an earlobe of the first ear. In this example, the second electrode 122 may be incorporated into the ear cup of a headset. Alternatively, the electrode 122 may be a discrete electrical contact which the user attaches to the back of their earlobe.

According to an example, the system 50 may further include a sensor 180 configured to measure a biometric property of the user. The sensor may be embedded into earpiece 100 as shown in FIG. 2. The sensor 180 may be a discrete device electrically connected to earpiece 100. The electrical connection may be wired or wireless. The second point in time may be adjusted according to the biometric property. The biometric property may be any property which would impact the rate of optimum application of VNS. The biometric property may be heart rate variability. The biometric property may be respiration rate. For example, as the respiration rate of the user decreases over time, the rate guided breathing audio cues and corresponding VNS may similarly decrease. In addition to the second point in time, any other point in time of the audio therapy regimen may be adjusted according to the biometric property.

According to an example, the system 50 may further include a user interface 190 configured for the user to input one or more personal characteristics, as shown in FIG. 2 (not to scale). The user interface 190 may be a discrete device, such as a smartphone, electrically connected to earpiece 100. The user interface 190 may include one or more buttons, one or more knobs, a processor, a memory, and/or a display screen. The electrical connection may be wired or wireless. These personal characteristics may include weight, age, or any other characteristics which would impact the rate of optimum application of VNS. The time period between the first point in time and the second point in time may be adjusted according to the one or more personal characteristics. In addition to the second point in time, any other point in time of the audio therapy regimen may be adjusted according to the biometric property.

In another aspect, and with reference to FIG. 2, an earpiece 100 for providing VNS to a user is provided. The earpiece may include an audio transducer 170 disposed within hollow passage 104. The audio transducer 170 may be configured to emit a first audio cue from the audio transducer at a first point in time. The first audio cue may prompt the user to inhale. The audio transducer 170 may be configured to emit a second audio cue from the audio transducer 170 at a second point in time. The second audio cue may prompt the user to exhale. The earpiece 100 may further include a first electrode 120. The first electrode 120 may be configured to form a first electrical contact with an ear canal, tragus, or concha of a user. The first electrode 120 may be further configured to deliver a vagus nerve stimulation signal at the second point in time.

According to an example, the earpiece 100 may further include a second electrode 122 configured to form a second electrical contact with the user. According to another example, the earpiece 100 may further include a sensor 180 configured to measure a biometric property of the user.

Turning now to FIG. 2 in more detail, FIG. 2 shows an example earpiece 100 including an ear tip that is configured to fit at least partially into a person's ear canal and a retaining structure configured to hold the ear tip in place when worn. The following should be viewed in light of FIG. 2. Earpiece 100 can include body 102, and hollow passage 104, and retaining legs 106. Although FIG. 2 shows retaining legs 106 as one embodiment of a retaining structure, this disclosure is not limited to such a configuration. Any type of retaining structure is contemplated. Alternatively, the retaining structure can be omitted altogether. The retaining legs 106 are optional.

Body 102 includes first end 108 and second end 110 opposite the first end 108. Second end 110 is proximate to the retaining legs 106. Body 104 further includes inner wall 107 extending between the first end 108 and the second end 110. Inner wall 107 defines and surrounds hollow passage 104 which can be configured to conduct sound waves. Body 102 also includes outer wall 112 connected to the inner wall 107 at the first end 108. Outer wall 112 tapers away from the inner wall 107 toward the second end 110. In example aspects, outer wall 112 is frustoconical in shape. As shown in FIG. 2, outer wall 112 tapers toward the second end 110 but does not necessarily reach the second end 110. In alternate embodiments not shown, outer wall 112 could extend to the second end 110 or beyond second end 110. Body 102 can be made of any suitable soft, flexible materials, including, for example, silicone, polyurethane, polynorbornene (e.g., Norsorex® material available from D-NOV GmbH of Vienna, Austria), thermoplastic elastomer (TPE), and/or fluoroelastomer.

Earpiece 100 includes electrically conductive elements 120, 122, and 124, which function as electrodes when positioned to contact skin within the ear, which generally is a stable environment offering good electrical and/or mechanical contact between skin and electrodes. Although FIG. 2 shows one particular configuration of an ear tip with electrically conductive elements 120 and 122 arranged on opposite sides of an outer surface of outer wall 112 (configured to fit at least partially into a person's ear canal), and electrically conductive element 124 arranged on body 102, this disclosure is not limited to such a configuration, and any number of electrically conductive elements can be placed in any configuration on earpiece 100 as long as the electrically conductive elements are arranged to contact skin and provide VNS within the ear when the earpiece is worn by a user. It should be appreciated that only two electrically conductive elements may be used to function as electrodes.

Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials).

Electrically conductive elements 120, 122, and/or 124 can be used to deliver an electrical signal to the ear, for example, for use in VNS. Electrically conductive elements 120, 122, and/or 124 can also function as physiological electrodes for detecting bioelectrical signals of an individual, including, for example, electroencephalogram (EEG), electrooculogram (EOG), electrocardiography (ECG), and electromyogram (EMG) signals, and may also be used to detect pulse rate, respiration rate, body temperature, sweat levels, and glucose, among other health parameters. Accordingly, electrically conductive elements 120, 122, and 124 may be used in place of or in conjunction with sensor 180.

Earpiece 100 may include an embedded integrated circuit, for example, inside the body 102. In examples, earpiece 100 is communicably coupled with an integrated circuit that is separate and remotely located, for example, in a computer or a mobile device. The integrated circuit can include a data processor, a memory, and a communication processor. Commands to be executed by the processor can be obtained via the communication processor. The communication processor facilitates wired or wireless communication for earpiece 100 and can be facilitated via one or more antennas, for example. The communication processor can facilitate communication with one or more networks or other devices, for example, by using wireless methods that are known, including but not limited to Wi-Fi. Bluetooth, 3G, 4G, LTE, and/or ZigBee, among others. Earpiece 100 can further include an embedded power source (e.g., a battery) required to carry out various functionalities involving the integrated circuit and the one or more electronic components described herein.

Figure 3:
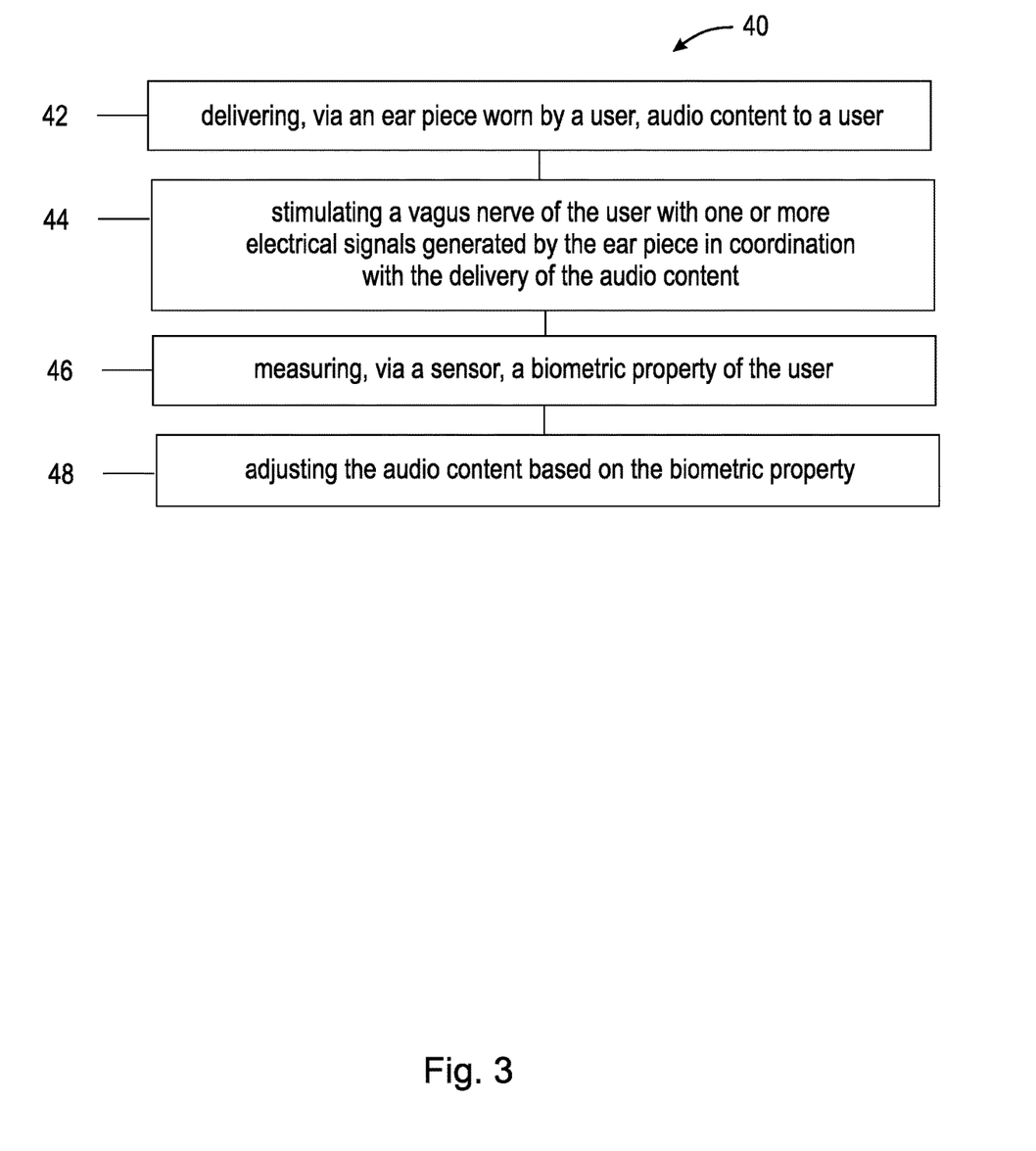
FIG. 3 is a flowchart of a further example of a method of providing VNS to a user.

In another aspect, and with reference to FIG. 3, a method 40 of providing VNS to a user is provided. The method 40 may include the steps of delivering 42, via an earpiece worn by a user, audio content to a user. The method 40 may include stimulating 44 a vagus nerve of the user with one or more electrical signals generated by the earpiece in coordination with the delivery of the audio content. Coordination between the one or more electrical signals and the delivery of the audio content may include any embodiments in which the vagus nerve is stimulated in accordance with the audio content. For example, if the audio content includes a series of audio tones, the vagus nerve may be stimulated simultaneously with the playback of each tone.

According to an example, the audio content may include guided breathing instructions prompting the user to adjust their respiration rate. The guided breathing instructions include audio cues to prompt the user to adjust their respiration rate. The step of stimulating 44 the vagus nerve of the user may further include stimulating the vagus nerve of the user in coordination with the audio cues. In another example, the audio content may be a series of binaural beats. The audio content may include any sounds, recordings, or soundtracks useful for audio therapy.

According to an example, the method may further include the step of measuring 46, via a sensor, a biometric property of the user. The method may further include the step of adjusting 48 the audio content based on the biometric property. The adjusted audio content may include guided breathing instructions. The adjusted audio content may include audio cues to prompt the user to adjust their respiration rate. Playback timing of the audio cues may be adjusted based on the biometric property.

According to an example, the earpiece may be further configured to adjust the guided breathing instructions based on a biometric property of the user measured by a sensor. The guided breathing instructions may further include audio cues to prompt the user to adjust their respiration rate. Playback timing of the audio cues may be adjusted based on the biometric property.

In another aspect, and with reference with FIG. 2, a system 50 for providing VNS to a user is provided. The system 50 may include an earpiece 100. The earpiece may include an audio transducer 170. The earpiece 100 may include a first electrode 120. The earpiece may be configured to form a first electrical contact between the electrode 120 and an ear canal, tragus, or concha of a first ear of a user. The earpiece 100 may be further configured to deliver audio content to a user. The earpiece 100 may be further configured to stimulate a vagus nerve of the user with one or more electrical signals generated by the earpiece 100 in coordination with the delivery of the audio content. The system 50 may further include a second electrode 122 configured to form a second electrical contact with the user.

According to an example, the audio content may include guided breathing instructions prompting the user to adjust their respiration rate. The guided breathing instructions may include audio cues to prompt the user to adjust their respiration rate. The earpiece 100 may be further configured to stimulate the vagus nerve of the user in coordination with the audio cues.

According to an example, the system may further include a sensor 180. The sensor 180 may be configured to measure a biometric property of the user.

According to an example, the earpiece 100 may be further configured to adjust the audio content based on the biometric property. The adjusted audio content may be guided breathing instructions. The adjusted audio content may include audio cues to prompt the user to adjust their respiration rate. Playback timing of the audio cues may be adjusted based on the biometric property.

In another aspect, and with reference with FIG. 2, an earpiece 100 for providing VNS to a user is provided. The earpiece 100 may include an audio transducer 170. The audio transducer 170 may be configured to deliver audio content to a user. The earpiece 100 may further include a first electrode 120. The first electrode 120 may be configured to form a first electrical contact with an ear canal, tragus, or concha of a user. The first electrode 120 may be further configured to stimulate a vagus nerve of the user with one or more electrical signals generated by the earpiece 100 in coordination with the delivery of the audio content.

According to an example, the audio content may include guided breathing instructions prompting the user to adjust their respiration rate. The guided breathing instructions may include audio cues to prompt the user to adjust their respiration rate. The first electrode 120 may be further configured to stimulate the vagus nerve of the user in coordination with the audio cues.

According to an example, the earpiece 100 may be further configured to adjust the guided breathing instructions based on a biometric property of the user measured by a sensor. The guided breathing instructions may further include audio cues to prompt the user to adjust their respiration rate. Playback timing of the audio cues may be adjusted based on the biometric property.

The above-described examples of the described subject matter can be implemented in any of numerous ways. For example, some aspects may be implemented using hardware, software or a combination thereof. When any aspect is implemented at least in part in software, the software code can be executed on any suitable processor or collection of processors, whether provided in a single device or computer or distributed among multiple devices/computers.

The present disclosure may be implemented as a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While several inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Other implementations are within the scope of the following claims and other claims to which the applicant may be entitled.

What is claimed is:

1. A method of providing vagus nerve stimulation to a user, comprising the steps of:
prompting, via a first audio cue emitted by an earpiece worn by a user, the user to inhale at a first point in time;
prompting, via a second audio cue emitted by the earpiece, the user to exhale at a second point in time; and
stimulating a vagus nerve of the user with a first electrical signal generated by the earpiece at the second point in time.

2. The method of claim 1, further comprising the steps of:
prompting, via a third audio cue emitted by the earpiece, the user to inhale at a third point in time;
prompting, via a fourth audio cue emitted by the earpiece, the user to exhale at a fourth point in time; and
stimulating the vagus nerve of the user with a second electrical signal generated by the earpiece at the fourth point in time.

3. The method of claim 2, wherein a time period between the third and fourth points in time is greater than a time period between the first and second points in time.

4. The method of claim 2, further comprising the steps of:
prompting, via a fifth audio cue emitted by the earpiece, the user to inhale at a fifth point in time;
prompting, via a sixth audio cue emitted by the earpiece, the user to exhale at a sixth point in time; and
stimulating the vagus nerve of the user with a third electrical signal generated by the earpiece at the sixth point in time.

5. The method of claim 4, wherein a time period between the fifth and sixth points in time is greater than the time period between the third and fourth points in time, and wherein a time period between the third and fourth points in time is greater than a time period between the first and second points in time.

6. The method of claim 1, wherein the first audio cue is an inhalation recording and the second audio cue is an exhalation recording.

7. The method of claim 1, further comprising the step of measuring, via a sensor, a biometric property of the user.

8. The method of claim 1, wherein the second point in time is adjusted according to the biometric property.

9. The method of claim 1, further comprising the step of inputting, by the user via a user interface, one or more personal characteristics.

10. The method of claim 9, further comprising the step of adjusting a time period between the first point in time and the second point in time according to the one or more personal characteristics.

11. A system for providing vagus nerve stimulation to a user, comprising:
an earpiece comprising an audio transducer and a first electrode, the earpiece configured to:
form a first electrical contact between the electrode and an ear canal, tragus, or concha of a first ear of a user;
emit a first audio cue from the audio transducer at a first point in time to prompt the user to inhale;
emit a second audio cue from the audio transducer at a second point in time to prompt the user to exhale; and
deliver a vagus nerve stimulation signal to the user via the first electrode at the second point in time; and
a second electrode configured to form a second electrical contact with the user.

12. The system of claim 11, wherein the earpiece further comprises the second electrode.

13. The system of claim 11, further comprising a sensor configured to measure a biometric property of the user.

14. The system of claim 13, wherein the second point in time is adjusted according to the biometric property.

15. The system of claim 11, further comprising a user interface configured for the user to input one or more personal characteristics.

16. The system of claim 15, wherein a time period between the first point in time and the second point in time is adjusted according to the one or more personal characteristics.

17. The system of claim 11, wherein the first audio cue is an inhalation recording.

18. The system of claim 11, wherein the second audio cue is an exhalation recording.

19. The system of claim 11, wherein the earpiece is further configured to:
emit a third audio cue from the audio transducer at a third point in time to prompt the user to inhale;
emit a fourth audio cue from the audio transducer at a fourth point in time to prompt the user to exhale; and
deliver a second vagus nerve stimulation signal to the user via the first electrode at the fourth point in time.

20. The system of claim 19, wherein a time period between the third and fourth points in time is greater than a time period between the first and second points in time.

* * * * *